(12) United States Patent
Paulson et al.

(10) Patent No.: US 6,383,417 B1
(45) Date of Patent: May 7, 2002

(54) METHOD FOR INJECTION MOLDING A CURVILINEAR LENS

(75) Inventors: Roy V. Paulson, Temecula; Donald R. Reiterman, Hemet, both of CA (US)

(73) Assignee: Paulson Manufacturing Corporation, Temecula, CA (US)

( * ) Notice: Subject to any disclaimer, the term of this patent is extended or adjusted under 35 U.S.C. 154(b) by 0 days.

(21) Appl. No.: 09/404,557

(22) Filed: Sep. 23, 1999

Related U.S. Application Data

(62) Division of application No. 08/998,517, filed on Dec. 26, 1997, now Pat. No. 6,105,177.

(51) Int. Cl.$^7$ .............................................. B29D 11/00
(52) U.S. Cl. ...................................................... 264/1.1
(58) Field of Search ............................... 264/1.1, 328.1; 2/431, 436, 439

(56) References Cited

U.S. PATENT DOCUMENTS

| | | | |
|---|---|---|---|
| 4,055,379 A | 10/1977 | Winthrop | 351/171 |
| 4,271,538 A * | 6/1981 | Montesi et al. | 2/439 |
| 4,867,550 A | 9/1989 | Jannard | 351/47 |
| 5,365,615 A * | 11/1994 | Piszkin | |
| 5,581,822 A | 12/1996 | Tagyo | 2/428 |
| 5,617,588 A | 4/1997 | Canavan et al. | 2/437 X |
| 5,774,201 A | 6/1998 | Tackles | 351/159 |

OTHER PUBLICATIONS

Encon Eye Protection, 500 Series Goggle, 2 pages (1989).
Encon Eye Protection, 160 Series Goggle, 2 pages (1989).
U.S. Safety, The Legend, 2 pages (1993).

* cited by examiner

*Primary Examiner*—Mathieu D. Vargot
(74) *Attorney, Agent, or Firm*—The Maxham Firm

(57) ABSTRACT

Goggles for protecting the eyes of a wearer in ultrahazardous conditions. The goggles comprise a frame that seals to the face of the wearer so that the wearer's eyes are enveloped. An adjustable strap is attached to the goggles and goes around the head of the wearer in order to secure the goggles over the wearer's face. Indirect ventilation is utilized to eliminate fogging, and drains are used in the frame to evacuate trapped moisture, A curvilinear lens with multiple optical zones is secured within the frame of the goggles and angled for increased lower peripheral vision. The materials with which the goggles are constructed are capable of withstanding a temperature of at least about 550° F. for a minimum of five minutes without oozing or dripping or otherwise deforming.

3 Claims, 10 Drawing Sheets

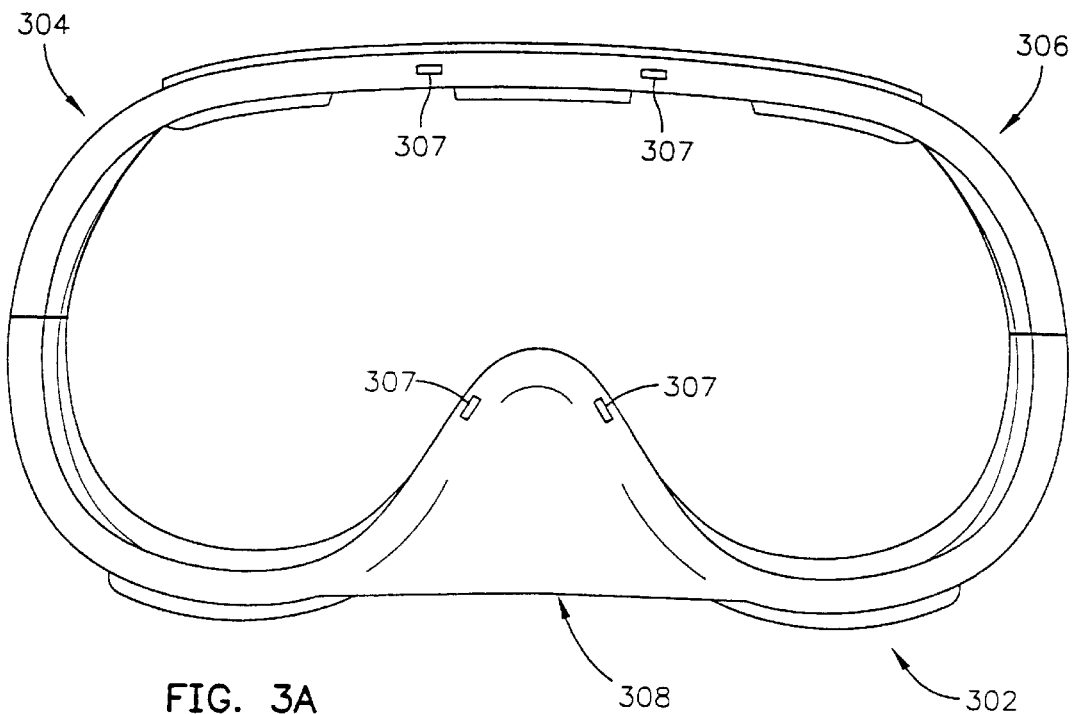
FIG. 3A
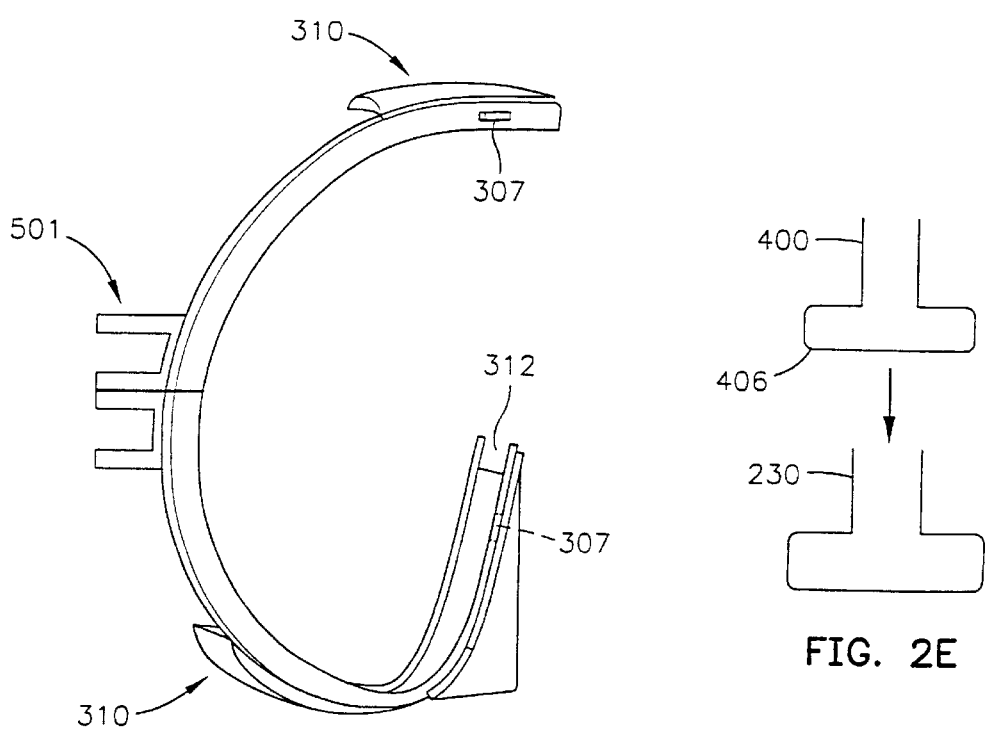
FIG. 3B
FIG. 2E

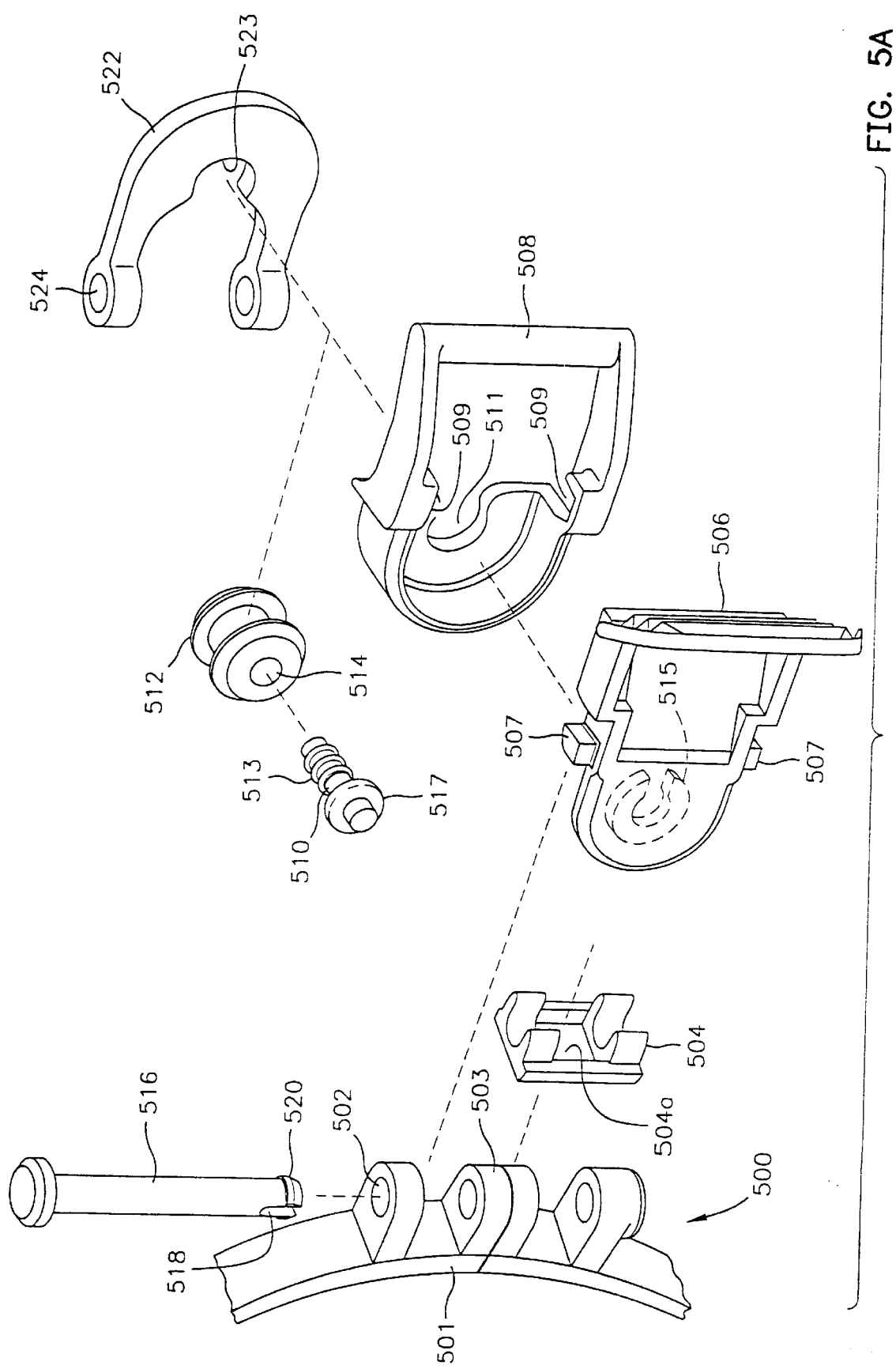

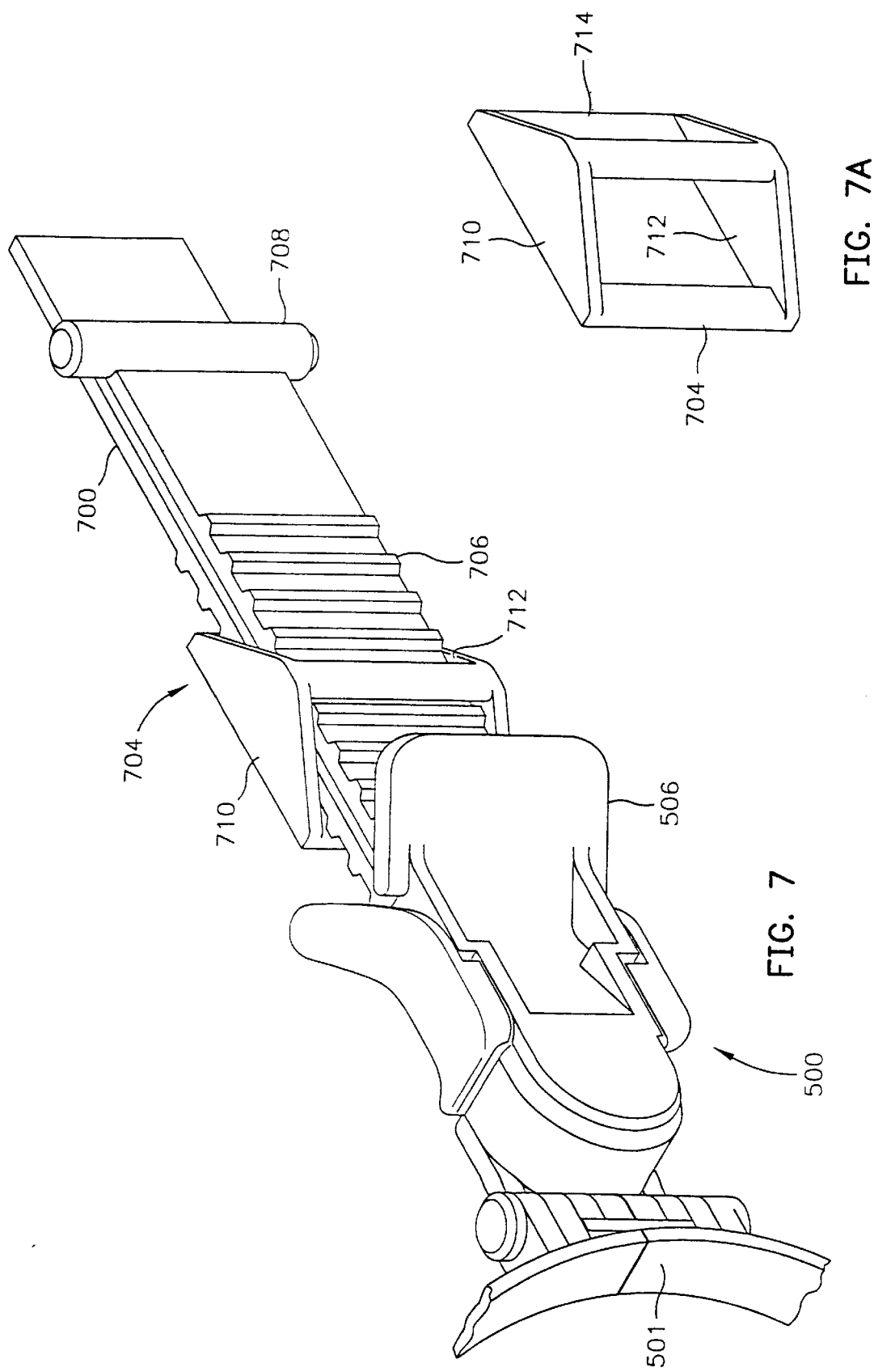

US 6,383,417 B1

METHOD FOR INJECTION MOLDING A CURVILINEAR LENS

CROSS-REFERENCE TO RELATED APPLICATION

This application is a division of application Ser. No. 08/998,517, filed Dec. 26, 1997, now U.S. Pat. No. 6,105,177, issued Aug. 22, 2000.

BACKGROUND OF THE INVENTION

1. Field of the Invention

This invention relates generally to protective eye wear and more particularly, for example, to goggles that protect the eyes of a firefighter from ultra-hazardous conditions.

2. Discussion of the Prior Art

When it is necessary to work in high temperature hazardous conditions such as those encountered by a firefighter, precautions to protect the firefighter's eyes become a necessity. Many different designs for eye protection under such severe high temperature conditions have been proposed. The eye protection previously known generally seeks to protect an individuals entire face against the hazardous conditions by using a heat-resistant face shield.

Little attention has been given to specifically protecting a user's eyes from high temperature hazardous conditions by using a pair of goggles. To date, no goggles exist which are designed for the purpose of meeting these high temperature hazardous conditions. This is important because goggles, as opposed to a face shield, are quicker and easier to use, can easily be adapted for use with a filter or respirator device, and provide enhanced eye protection. For the foregoing reasons, there is a need, especially for firefighters, for goggles that offer superior eye protection, overcome the shortcomings of currently available goggles, and enhance visibility.

SUMMARY OF THE INVENTION

Broadly speaking, the present invention is directed to an apparatus that satisfies the need for high temperature-resistant goggles that protect the wearer's eyes from ultra hazardous conditions, including extremely high temperatures and foreign materials which might otherwise impair the wearer's vision.

The goggles of this invention primarily comprise an assembly of four main elements: a frame, a lens, a bezel, and a strap. The frame is used in conjunction with the bezel and the lens to protect the eyes of the wearer, and the strap is used to secure the goggles in place. These goggles are: designed to form a comfortable fit and seal against the wearer's nose and face; configured to prevent moisture from accumulating on the inside of the goggles; configured to prevent foreign materials from entering from outside the goggles, and; designed to allow the goggles wearer to easily fit the goggles to his face while easily accommodating spectacles, when necessary, normally worn close to the user's face. The unique frame design allows the goggles to collapse flat, with the exception of the lens, for easy storage in a small space, such as a pocket, when not in use.

In one embodiment, the lens used in the goggles is curved and provides multiple optical zones integral therewith for enhanced undistorted vision. The frame securely holds the lens in place over the wearer's eyes. A bezel is attached to the frame. Opening covers are coupled to the bezel and cooperate with dams formed around the openings in order to prevent water or other undesirable matter from entering the interior of the goggles when they are on the wearer's face. The bezel includes an attachment which cooperates with the strap to adjustably secure the goggles in place on the wearer's face.

BRIEF DESCRIPTION OF THE DRAWING

The objects, features, and advantages of the present invention will become better understood with regard to the following description and appended claims, when read in conjunction with the accompanying drawing, wherein:

FIG. 2E depicts a T-shaped lens section and a T-shaped goggle frame section;

FIG. 3A depicts the front of the bezel of the goggles including a nose guard used in another, and preferred, embodiment of the present invention;

FIG. 3B is a perspective view of a first strap end of the bezel used with the goggles of FIG. 3A;

FIG. 5A is a perspective exploded view of the elements which, when assembled, constitute a preferred embodiment of an attachment device portion of the invention for the strap of the goggles of the invention;

FIG. 7 is a perspective view of a preferred embodiment of the strap used in conjunction with the attachment device of FIG. 6; and FIG. 7A is a detail of a retainer clip employed with the strap of FIG. 7.

DETAILED DESCRIPTION OF THE PREFERRED EMBODIMENTS

Figure 1:
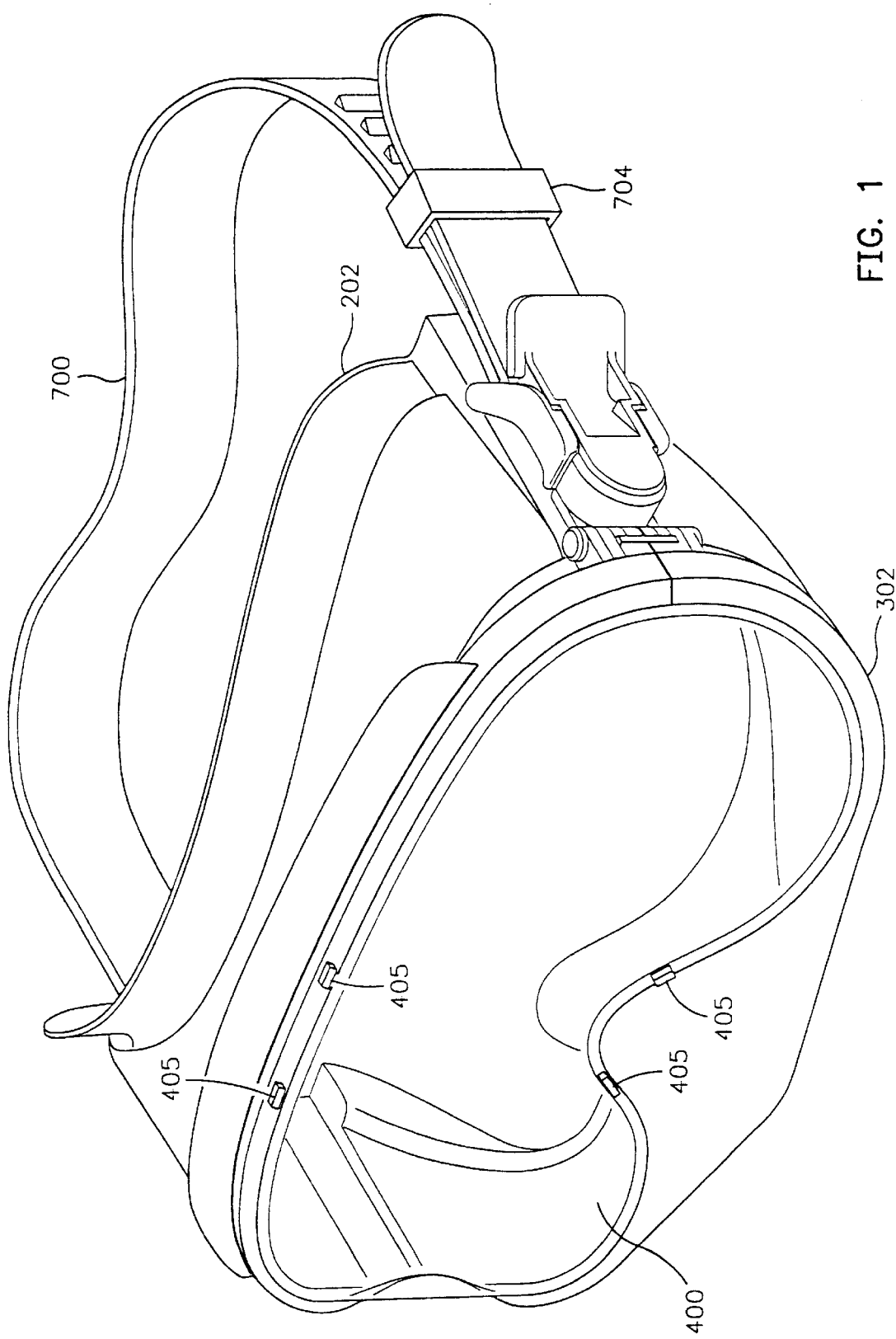
FIG. 1 is a perspective view of goggles constructed in accordance with one embodiment of the present invention.

With reference now to the drawing, and more particularly to FIG. 1 thereof, there is shown a perspective view of a preferred embodiment of the assembled goggles of the present invention. Generally, the goggles fit completely over the eyes and surrounding facial area of the wearer and a strap is placed around the wearer's head or safety hat to secure the goggles to the wearer's face. The goggles shown in FIG. 1 utilize a flexible frame 202 which is used to disconnectably house a curvilinear lens 400. A semi-rigid bezel 302 is removably affixed to he flexible frame 202. A strap 700 is coupled to the bezel, allowing the goggles to be removably and adjustably secured to the face of the wearer when the strap is passed around the back side of the wearer's head. A strap retainer means 704 is used in conjunction with the strap in order to retain any loose ends of the strap.

In one embodiment, the frame 202, shown in detail in FIGS. 2A through 2D, has six sides integral thereto: a lens side 206 opposite to a flange side 204; an upper side 208 opposite to a lower side 222; and a first strap end 212 opposite to a second strap end 214. The frame 202 is made of a flexible material to allow the frame to be comfortably fitted to the face of the wearer, and to allow the frame to be selectively, substantially collapsed for storage.

Figure 2A:
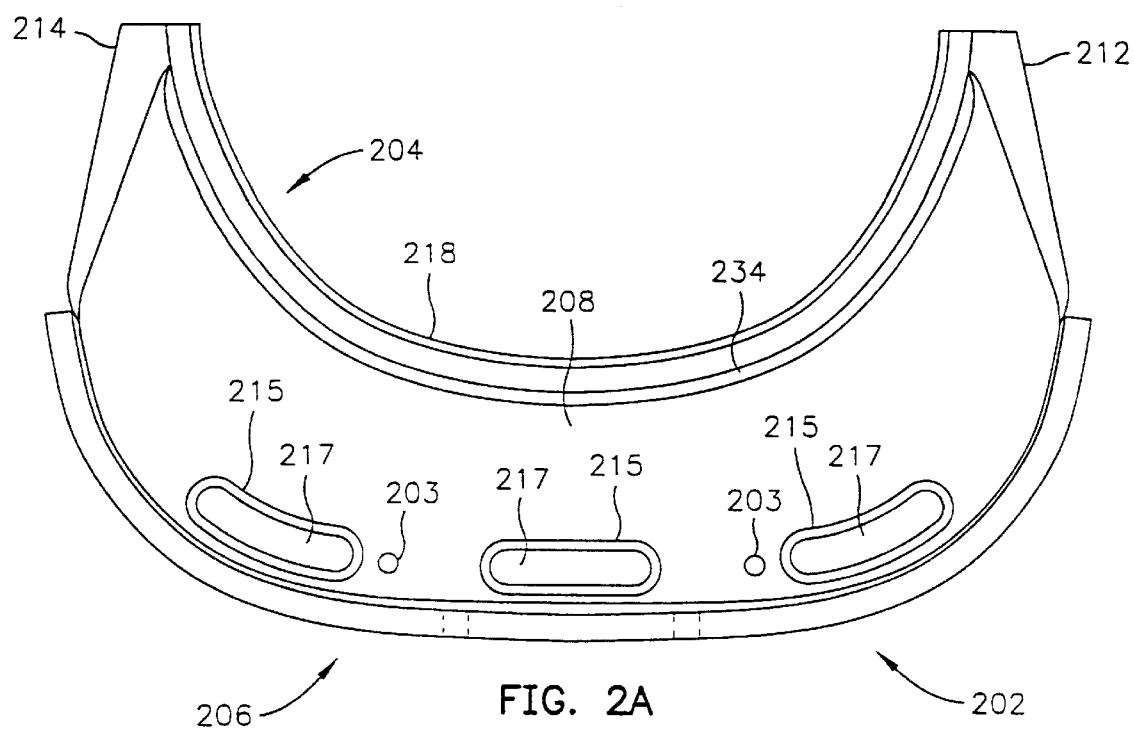
FIG. 2A depicts a plan view of the frame of the goggles of FIG. 1 as viewed from above.
Figure 2B:
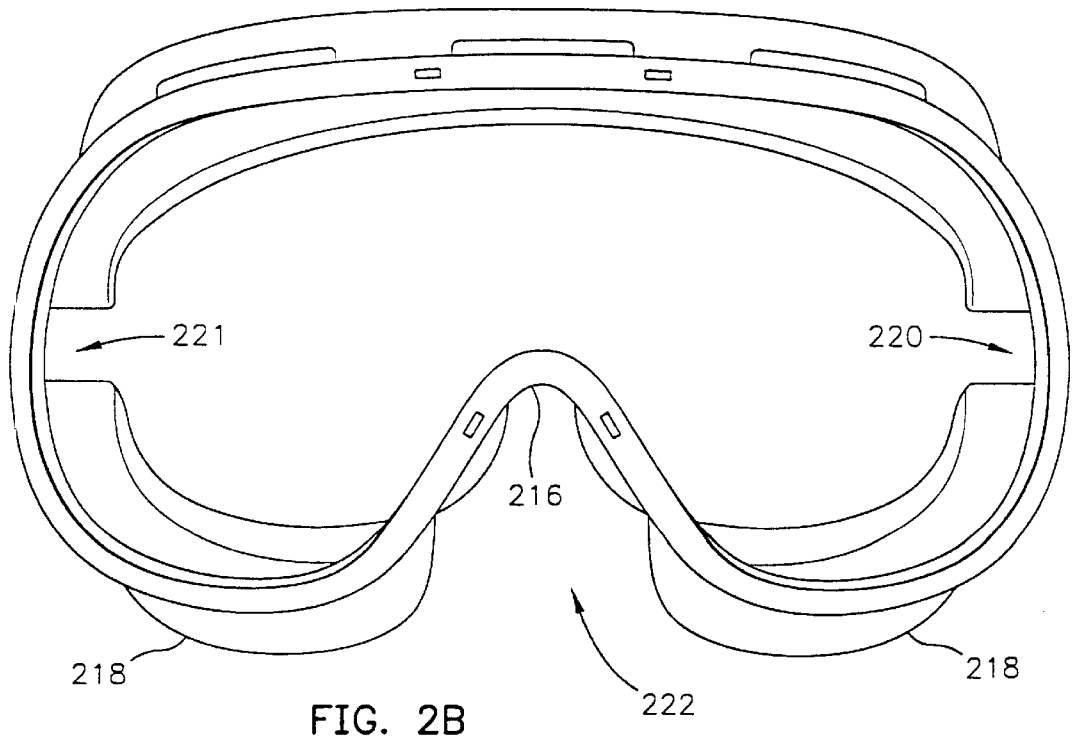
FIG. 2B shows a lens-side view of the frame of the goggles of FIG. 1.
Figure 2C:
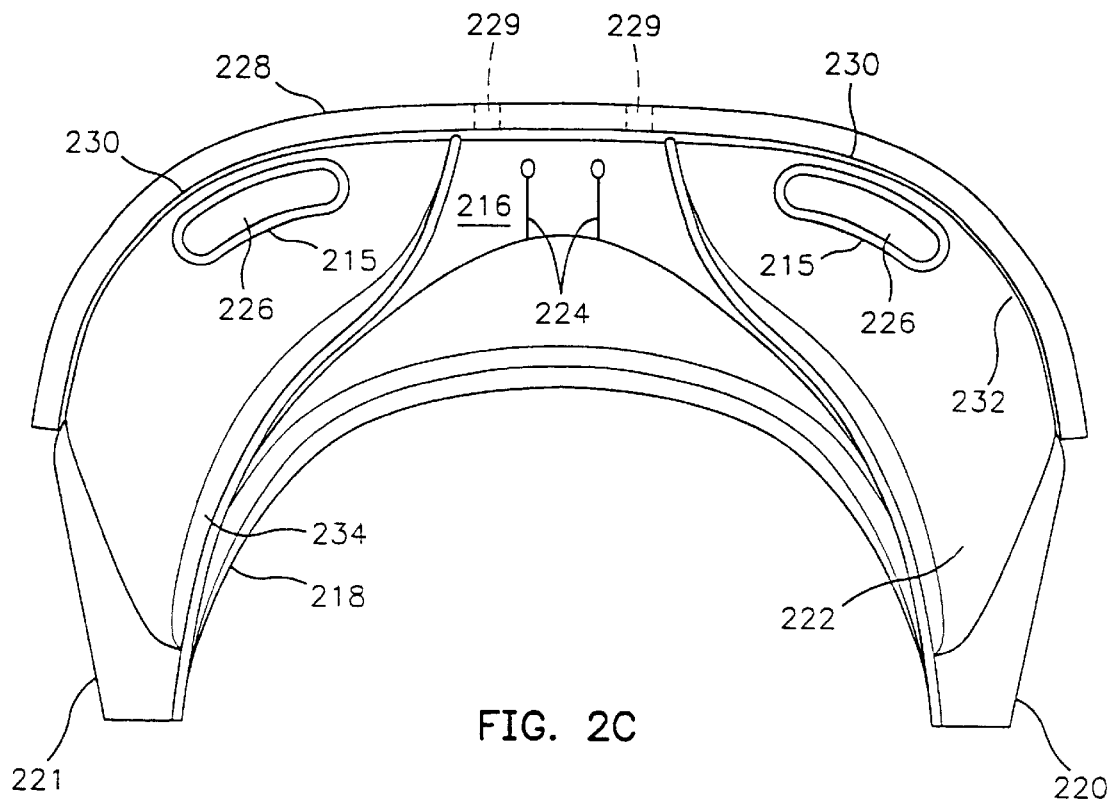
FIG. 2C illustrates a plan view of the frame of the goggles of FIG. 1 as viewed from below.

The lens side 206 of the frame 202 incorporates a lens surround area 228 as shown in FIG. 2C. The lens surround area incorporates lens surround slots 229 through which lens tabs 405, discussed below, extend. The tabs and a lens retention channel 230 capture the lens 400 by its perimeter 406 (shown in FIGS. 4A and 4B) and secures the lens to the frame 202. However, the lens could also be secured to the lens surround area 228 by other suitable means such as snaps, adhesives, or by molding the lens directly into the frame.

Figure 2D:
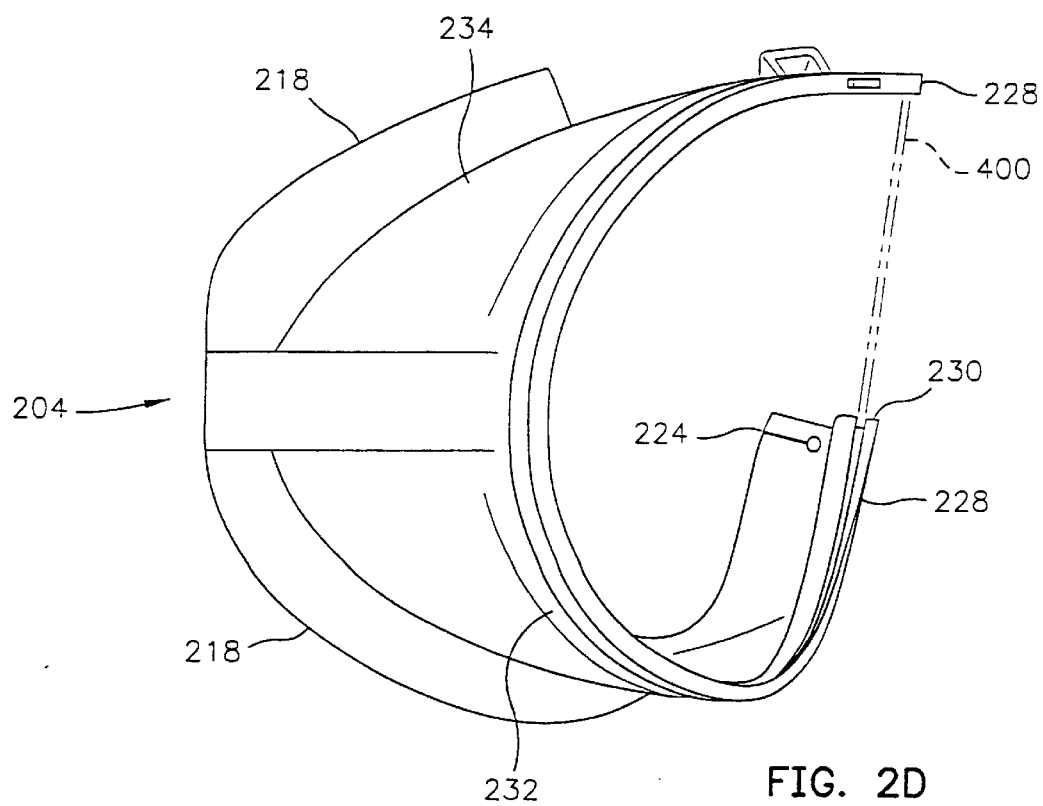
FIG. 2D is a plan view of a first strap end of the frame of the goggles of FIG. 1.

Located opposite to the lens side 206 is the flange side 204 as shown in FIG. 2D. A face flange 218 is integrated with the flange side 204 in order to assure proper sealing of the goggles to the wearer's face. For cold weather applications, a foam seal (not shown) may be used and secured by adhesive or many types of fasteners, including hook-and-loop snaps or friction, to the face flange 218 to enhance the seal. The lens side 206 and the flange side 204 are separated by the upper side 208 shown in FIG. 2A, the lower side 222 shown in FIG. 2C, the first strap end 212, and the second strap end 214, both shown in FIG. 2A.

In one version of the present invention as shown in FIG. 2C, the lower side 222 of the frame 202 has second openings 226 which are surrounded by dams 215. A nose section 216 (shown in FIG. 2B) is formed in the lower side 222 in order to accommodate the nose of the wearer and to assure that the goggles seal properly atop the wearer's nose. The nose section 216 cooperates with the face flange 218 to complete a proper seal to the wearer's face. At least one nose release 224 is integral to the nose section and allows for a more comfortable fit by allowing greater flex in the nose section while maintaining a tight seal. A first gutter 234 is formed into the frame 202 and is juxtaposed to the face flange 218. The gutter channels liquid and debris that strike the frame away from the face flange The upper side 208 as shown in FIG. 2A has first opening 217 in one version of the invention which are surrounded by the same kind of dams 215. A second gutter 232 is integral to the frame and juxtaposed to the lens surround area 228. The upper side 208 is separated from the lower side 222 by the first strap end 212 and the second strap end 214.

Completing the frame in one embodiment are first and second strap ends 212 and 214, respectively, each accommodating a first and second channel 220 and 221, respectively, shown in FIGS. 2B and 2C. As shown in FIGS. 2C and 2D, both channels extend from the second gutter 232 toward the flange side 204, bisecting the first gutter 234 and the face flange 218. In the preferred embodiment, the channels 220 and 221 are designed such that the frame 202 can easily be slid over the eyeglasses of a wearer without the wearer having to remove the eyeglasses before fitting the goggles.

Figure 4A:
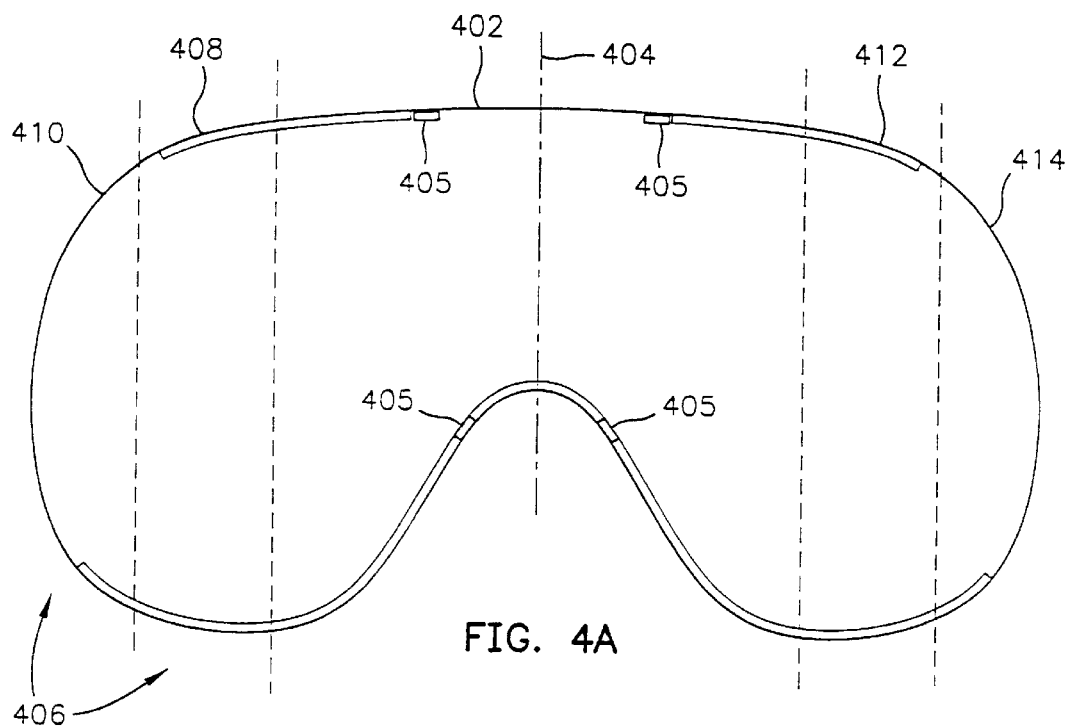
FIG. 4A is a front view of the lens of the goggles of FIG. 1.

As indicated above and as shown in FIG. 2D, the curvilinear lens 400 is captured about its lens perimeter 406 shown in FIG. 4A in one embodiment by the lens retention channel 230. Preferably, the lens perimeter and the lens retention channel are both "T" shaped, thereby allowing the lens perimeter to be securely cradled by the lens retention channel so that the lens 400 will not separate from the frame 202 if impacted. As shown in FIG. 2E, sections of the lens retention channel 230 are T-shaped to slidably receive the T-shape sections of the lens perimeter 406. This "cradling" allows the lens to seal to the frame and prevents any foreign substance from passing between the lens 400 and the frame. Furthermore, the lens perimeter 406 preferably has tabs 405 extending substantially perpendicular therefrom and away from an outer surface 401 of the lens 400, the outer surface and the tabs 405 being shown in FIGS. 4A and 4B. Although four such tabs are shown, several tabs may be spaced around the periphery.

Figure 4B:
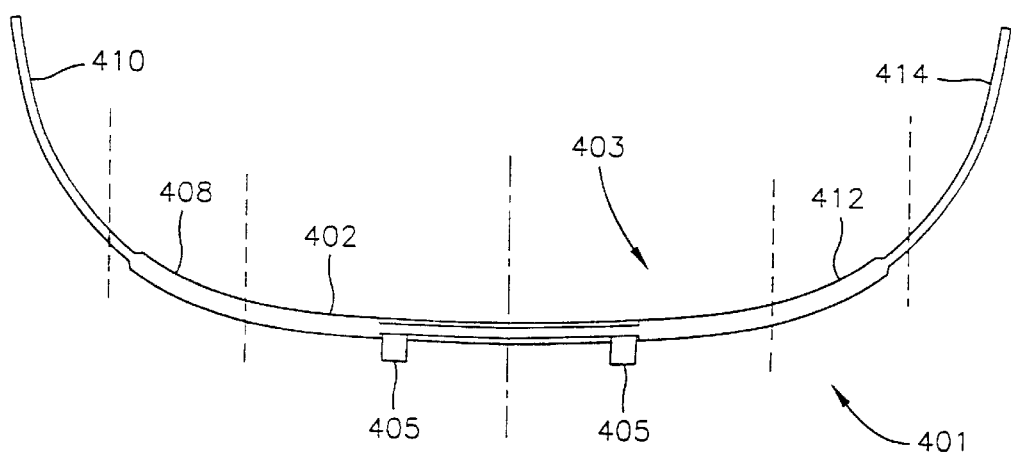
FIG. 4B is a view of the lens of FIG. 4A as viewed from above.

In one version of the invention shown in FIG. 4B, the curvilinear lens 400 has an inner surface 403 and an outer surface 401. The inner surface and the outer surface may be substantially parallel, or may converge or diverge. In one embodiment, the distance between the inner and outer surface may vary between approximately 0.08 inches and 0.100 inches. Preferably, the inner surface 403 is treated with an anti-fog substance and the outer surface 401 is treated with an abrasion-resistant substance. The shape of the lens 400 allows a unique shape for the goggles to be achieved, thereby substantially reducing and preferably eliminating distortion between the multiple optical zones of the lens and allowing the goggles to be placed on the face of the wearer without the wearer having to first remove his spectacles which, for goggles wearers with corrected vision, may be a necessity. For example, a firefighter may have to quickly put the goggles on over his glasses while threatened by flames in zero-visibility situations.

Generally, the lens 400 may have five curvilinear optical zones each distinguished by broken lines in FIGS. 4A and 4B. These optical zones comprise: a curvilinear central optical zone 402 on either side of center line 404; a first and a second curvilinear side optical zone 408 and 412, respectively; and a first and a second curvilinear rear optical zone 410 and 414, respectively. The lens 400 extends vertically between the lower side 222 and the upper side 208 of the frame 202, and horizontally between the first and second strap ends 212 and 214. In one embodiment, shown in FIG. 2D, the lens 400 is canted within the frame 202 in order to increase the lower peripheral vision of the wearer and allow the wearer to see the ground immediately before him.

When properly positioned in the frame 202, the central optical zone 402 of lens 400 is substantially centered within the lens surround area 228. As shown in FIGS. 4A and 4B, the first side optical zone 408 is contiguous to the central optical zone 402 and is positioned between the central optical zone and the first rear optical zone 410. Preferably, the two side optical zones 408 and 412 are hyperbolically curved in a direction substantially perpendicular to a vertical centerline 404. The first side optical zone 408 is also contiguous to the first rear optical zone 410. The first rear optical zone is positioned between the first side optical zone 408 and, when mounted in the frame, the first strap end of the frame. The second side optical zone 412 is also contiguous to the central optical zone and is positioned between the central optical zone and the second rear optical zone 414. The second side optical zone is contiguous to the second rear optical zone which is positioned between the second side optical zone and, when mounted in the frame, the second strap end of the frame The radius of curvature for each curvilinear zone discussed—at the point of contiguity to the respective abutting zone—is equal to the radius of curvature of the abutting zone. This equal radius of curvature at the point of contiguity substantially eliminates optical distortion that might otherwise be perceived by the wearer due to the transition from one zone to another. Although the use of only one lens is discussed in conjunction with the preferred embodiment, multiple lenses could be used in an alternative embodiment. Similarly, any number of curvilinear optical zones could be integral to the lens 400.

One method of making the curvilinear lens is by injection molding using an optically transparent material. A preferred method uses a mold having a tool die capable of being parted. The tool die has walls that define a hollow that is shaped to generally reflect a negative embodiment of the curvilinear lens. When the optically transparent material reaches a stable, substantially non-fluid state, the lens is removed from the die. Another molding method assists the optically transparent material in reaching the stable, substantially non-fluid state.

The detail of the bezel 302 of a second embodiment of the invention is shown in FIGS. 3A though 3D. In this embodiment, the bezel 302 is two-piece and semi-rigid, and cooperates with the lens retention channel 230 to further secure the lens 400 in the frame 202. In the preferred embodiment, a bezel attachment channel 312 is formed into the bezel 302 and tightly cradles the lens surround area 228, which includes lens retention channel 230, which in turn tightly cradles the perimeter 406 of the lens 400. Slots 307 are included in the bezel as shown in FIGS. 3A and 3B and engage tabs 405 extending from lens 400. This preferred attachment arrangement allows the bezel 302 to be removably attached to the lens surround area 228 of the frame 202 while preventing separation between the frame and the lens 400. Alternatively, the bezel 302 may be attached to the frame by adhesive, snaps, or molded fitting, for example. The two-pieces of the bezel are coupled together by a bezel clip 504 being slid over a two-piece center projection 503 of a bezel clip receiver as shown in FIG. 5.

Figure 3C:
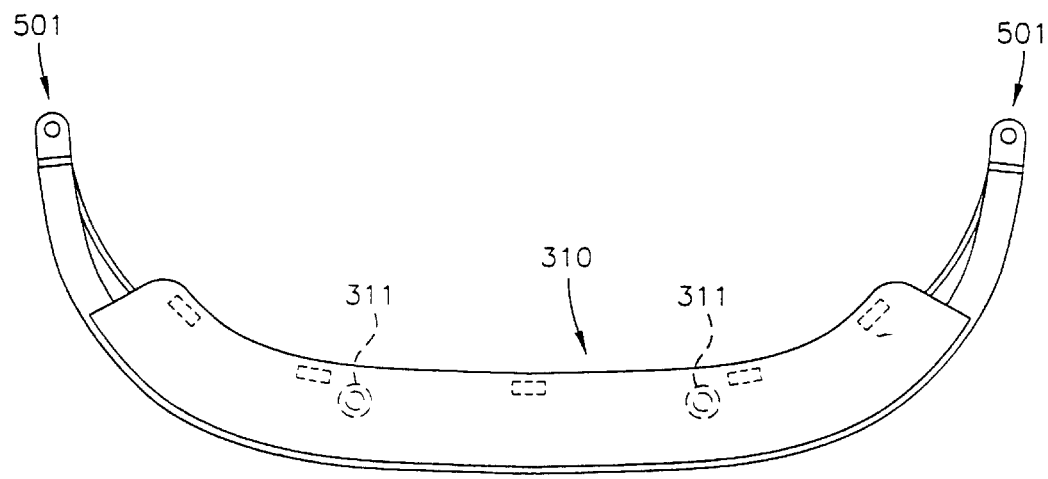
FIG. 3C is a plan view of the bezel of FIG. 3A as viewed from above.
Figure 3D:
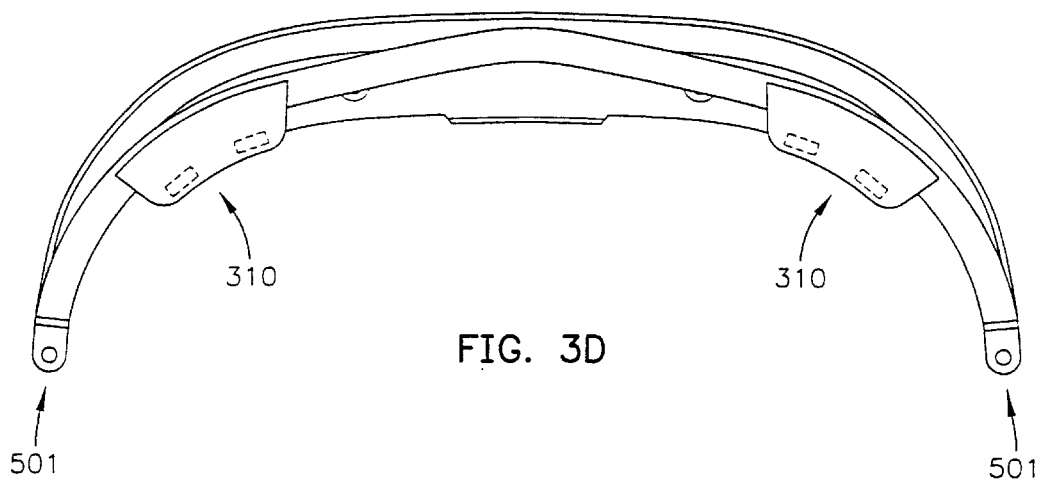
FIG. 3D is a plan view of the bezel of FIG. 3A as viewed from below.

The bezel 302 has a first end 304 and a second end 306 that cooperate with the strap 700 (FIG. 7) and an attachment means used to hold the two-piece bezel together and secure the goggles to the face of the wearer. In one embodiment, opening covers 310 having set-off tabs are coupled to the bezel 302 and are positioned in such a way that these opening covers extend over first openings 217 and second openings 226 when the bezel 302 is attached to the frame 202. The set-off tabs keep the openings clear by preventing sealed contact with the opening covers. The opening covers also cooperate with dams 215 which surround the first and second openings 217 and 226, respectively, to prevent foreign matter from contacting the eyes of the wearer. To prevent a gap from opening up between the frame 202 and the opening covers 310 which cover first openings 217, barbed fasteners 311 shown in FIG. 3C and integral to the opening covers 310 button to holes 203 shown in FIG. 2A. This arrangement allows the bezel 302 to be removed from the frame 202 to facilitate replacement of the lens 400, if necessary. Although barbed fasteners 311 are preferred, any detachable fastening arrangement may be used, such as snaps, integral molding, tabs, or the like. Optionally, a nose cover 308 as shown in FIG. 3A can be integrated with the bezel 302 in a position to cover the nose of the wearer when the goggles are positioned over the eyes of the wearer.

Preferably, the goggles are secured to the face of the wearer by placing a strap around the head of the goggles wearer. However, the strap may be placed around a hat worn by the goggle wearer. In either case, the strap, shown in FIG. 7, is attached to the bezel 302 of the goggles. However, removably or permanently attaching the strap directly to the frame 202 would also be acceptable. The strap may be flat or cylindrical, and is preferably molded from liquid silicone elastomers in the embodiment, but could also be constructed from rubber, plastic, fiber, or like materials. One end of the strap 700 cooperates with an attachment means, such as that shown in FIGS. 5A–5C, coupled to the first end 304 of the bezel 302. The other end of the strap cooperates with another attachment means which is attached to the second end 306 of the bezel.

A preferred attachment means for use with the strap in securing it to bezel 302 uses two attachment devices 500 shown in FIG. 5A. One strap attachment device 500 couples to the first end 304 of the bezel 302 and another such device couples to the second end 306 of the bezel.

Figure 5B:
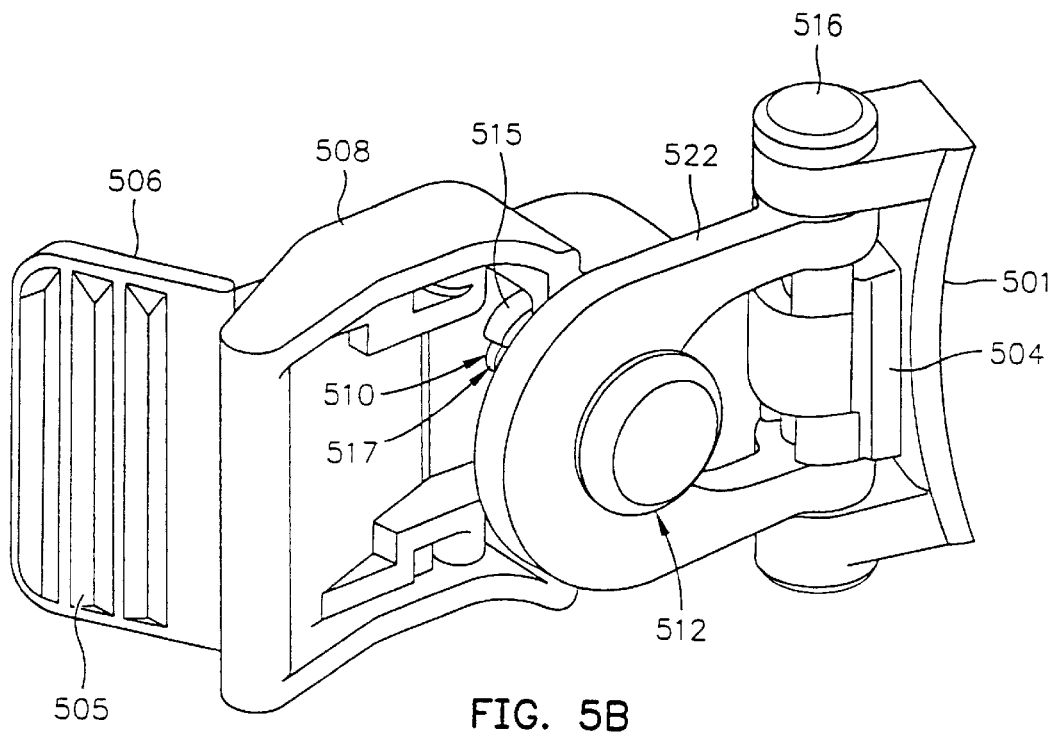
FIG. 5B is a perspective inside view of the assembled elements of the attachment n device of FIG. 5A.
Figure 5C:
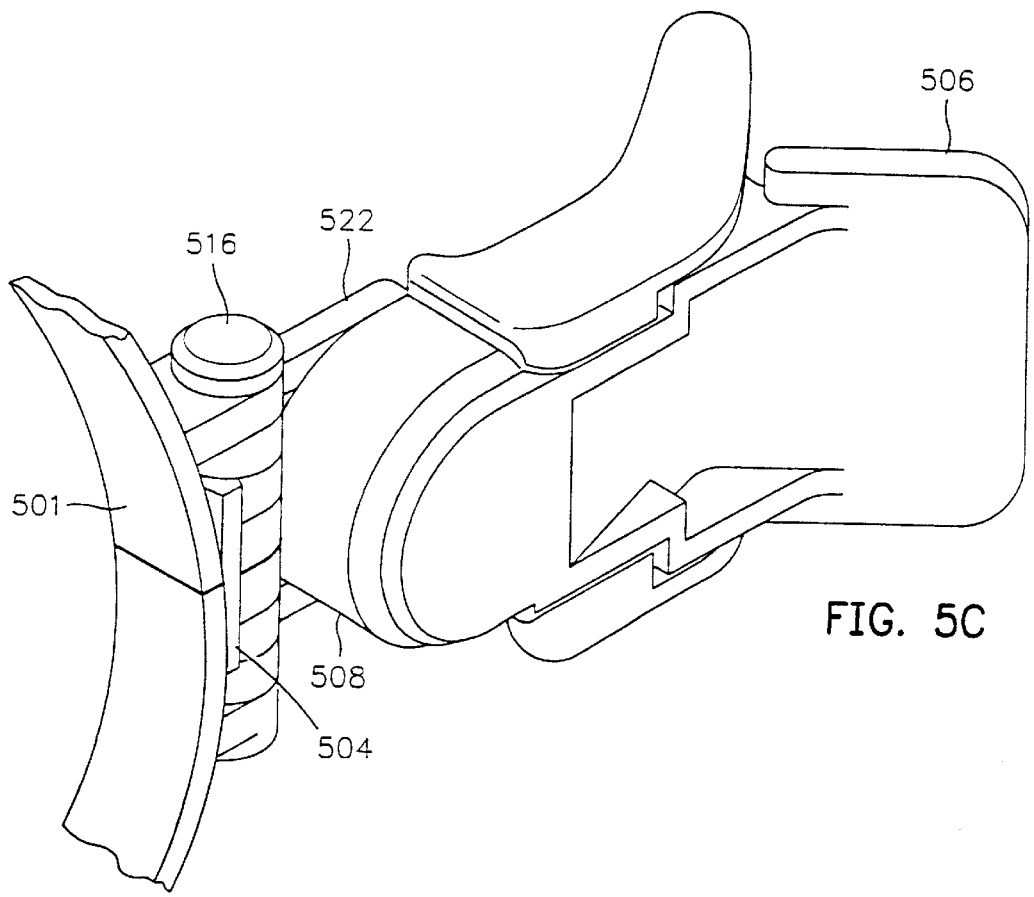
FIG. 5C is a perspective outside view of the assembled elements of the attachment device of FIG. 5A.

To fully appreciate integral attachment device 500, reference is made to FIGS. 5A–5C. FIG. 5A illustrates the elements of the attachment device connected to the bezel clip receiver 501 and including a bezel clip 504. The bezel clip receiver 501 has a plurality of receiver bores 502 which are substantially coaxial. The bezel clip 504 is removably snapped onto the bezel clip receiver 501 which is integral to the bezel as opening 504a receives the center projection 503. A ratchet pawl 506 having mounting protrusions 507 is also shown, as is a strap hanger 508 having first reliefs 509 and a second relief 511.

FIG. 5A also shows a pivot axle 512 having an axle bore 514. A pivot axle plug 510, having ridges 513, is inserted into the axle bore 514. The plug 510 may be a flexible elastomer plug that allows both compressive and tensile movement of the plug. The pivot axle plug 510 is sized and positioned so that the ridges 513 are removably held within the axle bore. A protruding portion 517 (shown in FIG. 5A) of the pivot axle plug 510 may protrude beyond one end of the pivot axle 512 when the pivot axle plug is fully inserted into the pivot axle.

The pivot axle 512 is rotatably coupled within the second relief 511 of the strap hanger 508, and the protruding portion 517 of the pivot axle plug 510 rotatably engages locking arms 515 (shown in FIG. 5A) of the ratchet pawl 506. The interlocking of locking arms 515 with the pivot axle 512 causes the mounting protrusions 507 to be securely held within the first reliefs 509 of the strap hanger 508. Mounting the ratchet pawl 506 it thing fashion allows it to be cantilevered when a pressure is applied to ribs 505 (shown in FIG. 5B) in a direction substantially perpendicular to the surface from which the ribs extend, compressing the pivot axle plug 510.

FIG. 5B shows the assembled relationship of the pivot axle 512, the strap hanger 508, and the ratchet pawl 506. A pivot plate 522 is rotatably coupled with the pivot axle 512. This rotatable coupling occurs when plate relief 523 shown in FIG. 5A is slid into place around the pivot axle 512. Ridges 513 are used on the pivot axle plug 510 which is inserted into the axle bore 514 of the pivot axle 512, and the pivot axle allows the pivot plate 522 to be "snapped" into place around the pivot axle. The pivot plate 522 is rotatably coupled to the bezel clip receiver 501 by placing pivot plate bores 524 (shown in FIG. 5A) in axial alignment with the receiver bores 502.

A hinge pin 516 is used to rotatably couple the bezel clip receiver 501 with the pivot plate 522. Note that in FIG. 5B the ratchet pawl 506 is securely held within the strap hanger 508 by the interlocking cooperation of the protruding portion 517 of the pivot axle plug 510 and the locking arms 515 of the ratchet pawl. The pivot axle 512 serves to rotatably secure the strap hanger 508 to the pivot plate 522. In turn, the pivot plate 522 is rotatably coupled to the bezel clip receiver 501. The bezel clip 504 cradles the hinge pin 516. FIG. 5C shows a perspective view of the assembled device, further illustrating the relationship of the cooperating elements as shown in this embodiment.

Figure 6:
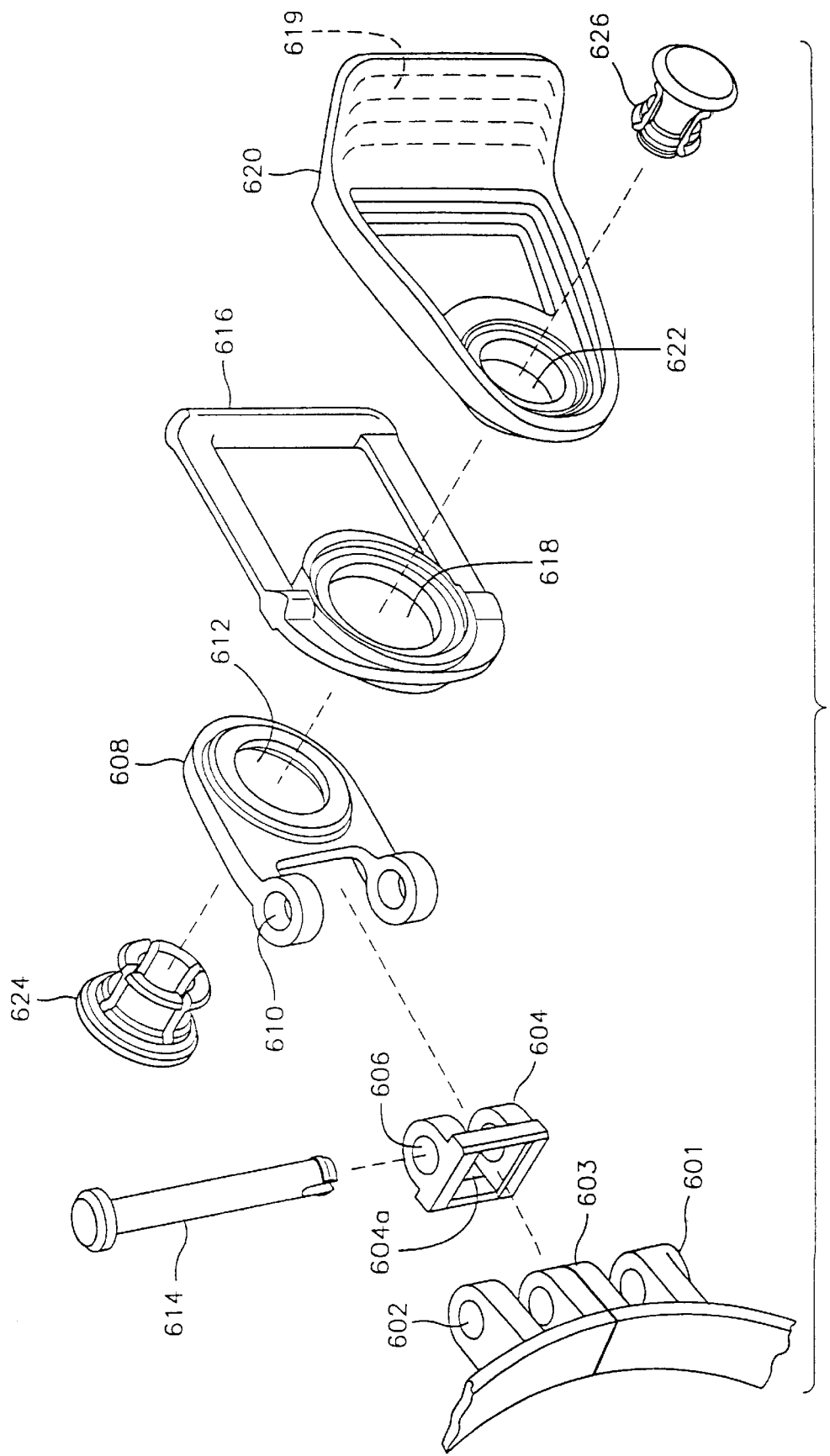
FIG. 6 is a perspective exploded view of an alternative embodiment of attachment device portion of the invention for the strap of the goggles of the invention.

An alternate embodiment 600 of the strap attachment device is shown in FIG. 6. A bezel clip receiver 601 having a plurality of receiver bores 602 is integral to one end of the bezel 302. Opening 604a of bezel clip 604 slides over protrusion 603 of the bezel clip receiver. A pivot mount 608 having a pivot bore 610 interlaces with the bezel clip 604 and the bezel clip receiver 601 so that receiver bores 602, the bezel clip bores 606, and the pivot bore 610 are all substantially coaxial when assembled. A hinge pin 614 engages receiver bores 602 of receiver 601, the bezel clip bores 606, and the pivot bores 610 so that the hinge pin and bores cooperate and allow for rotational displacement of the pivot mount 608. The pivot mount has a mounting bore 612 which cooperates with a strap hanger bore 618, which is integral to a strap hanger 616, and a ratchet pawl bore 622 which is integral to a ratchet pawl 620, to allow the strap to be adjusted when the goggles are fitted to the head of the wearer. The pivot mount mounting bore 612, strap hanger bore 618 and ratchet pawl bore 622 are interconnected by a removable pivot pin 624 which cooperates with a pivot retainer 626 which is removably connected thereto. Winged ribs 619 are formed on one side of the ratchet pawl 620 to allow easier displacement of the ratchet pawl.

A perspective view of one end of the strap 700 engaged by the attachment device 500, as shown in FIGS. 5A–5C, is illustrated in FIG. 7. As discussed above, each end of the strap engages a respective attachment device 500. However, FIG. 7 only shows one end of the strap engaging one version of an attachment device for clarity purposes. Ribs 706 are integral to the strap in one preferred embodiment and assist the strap 700 in being captured by the attachment device and in preventing unwanted adjustment of the goggles when they are worn by the user. The ratchet pawl 506 is shown in its resting position after engagement of the strap. Compression of the pivot axle plug 510 (FIG. 5A) provides the force to keep the ratchet pawl 506 in contact with the strap 700. A bar 708, integral to the strap 700, is shown in its preferred position relative to one end of the strap. This bar is intended to prevent the end of the strap from inadvertently disengaging from the attachment device 500 when the goggles are adjusted for fit by the wearer. A bar 708 is placed similarly to that shown at each end of the strap. Although it is preferred that the bar 708 be integral to the strap, the bar may be a separate device which is coupled to the strap and performs the same anti-disengagement function.

The typical retainer clip 704 which is used in conjunction with the strap is shown in FIGS. 7 and 7A. This retainer clip has a first side element 710 and a second side element 712. These side elements are interconnected in such a way that the strap 700 is permitted to pass between them, and allows for any loose end of the strap to be captured by the retainer clip. A side connector such as bars 714 would suffice for this interconnection as would any other suitably configured side connecting element.

In one embodiment, the invention described above is designed to meet the needs of a person who requires eye protection in ultra-hazardous conditions, and is specifically designed to meet the needs of a firefighter. The goggles are placed over the eyes of the firefighter, preferably prior to entering a hazardous condition. The frame 202 is specifically designed to fit over the spectacles, if any, of a firefighter without necessitating the removal of the spectacles when the goggles are either placed over the eyes or are removed from over the eyes of the firefighter. In the preferred embodiment, as shown in FIG. 1, the frame is also designed so that the goggle may be used in conjunction with a breathing device such as a respirator. In another embodiment, the nose cover 308 of the bezel 302 can be used to protect the nose of the wearer.

The goggles described above, in the preferred embodiment, are constructed of heat-resistant materials which may withstand minimum temperatures of about 550° F. for a minimum of five minutes without deforming. The first and second openings 217 and 226 allow indirect venting of the goggles and prevent fogging of the lens while allowing drainage of perspiration that might otherwise be trapped between the face of the wearer and the lens. Dams 215 which surround the openings 217 and 226 cooperate with opening covers 310 in order to prevent external materials from contacting the eyes of the wearer.

The unique design of the goggles frame eliminates interference with spectacles and allows the goggles to be placed over the eyes of the wearer and to be removed without the removal of the spectacles. The lens 400, as shown in one embodiment is canted within the frame in order to increase the lower peripheral vision of the wearer and allow the wearer to see the ground immediately before him. The cant referred to can be easily seen by referencing the side view of the frame 220 shown in FIG. 2D. Because the preferred embodiment is designed for firefighters, and because firefighters are customarily in areas where the footing is unstable and hazardous, increased lower peripheral vision is important. Preferably, the lens is injection molded and optically corrected to eliminate distortion at the inner face of the multiple optical zones.

Although the goggles have been described in considerable detail with reference to certain preferred versions thereof, other versions are possible. For example, in an alternate embodiment, the frame 202 may be strapped around or attached to the head gear of the goggles wearer. By attaching the goggles to the headgear of the wearer, the goggles may be securely held over the eyes of the wearer and removed by removing the helmet. Because other versions are anticipated, the spirit and scope of the appended claims should not be limited to description of the preferred versions contained herein. It is likely that improvements and modifications will occur to those who are skilled in this art which are within the spirit and scope of the accompanying claims.

What is claimed is:

1. A method for forming a curvilinear lens by injection molding, the method comprising the steps of:

using a tool die capable of being parted, the die having walls, said walls defining a hollow, said hollow shaped to generally reflect a negative embodiment of said curvilinear lens to be formed, said embodiment including:
a curvilinear first surface, said first surface corresponding to said inner surface of said lens;
a curvilinear second surface, said second surface corresponding to said outer surface of said lens;
a perimeter; and
multiple zones integral to said embodiment, said multiple zones comprising:
a central zone positioned at a center of said embodiment, said curvilinear second surface diverging with said curvilinear first surface about said central zone so that a thickness between said first surface and said second surface is maximized toward said center of said central zone;

curvilinear side zones separated by said central zone, said side zones comprising:
    a first side zone contiguous to said central zone; and
    a second side zone contiguous to said central zone; and curvilinear rear zones spaced from said central zone by said side zones, said rear zones comprising:
    a first rear zone contiguous to said first side zone, wherein said curvature of said first side zone is equal to a curvature of said first rear zone at said contiguous location; and
    a second rear zone contiguous to said second side zone, wherein said curvature of said second side zone is equal to a curvature of said second rear zone at said contiguous location;

the die being shaped and configured to provide a curvilinear lens having a shape minimizing optical distortion at each contiguous interface between adjacent zones of said lens;

flowing a fluid optically transparent material into said hollow of said die to form said curvilinear lens;

allowing said transparent material to obtain a stable substantially non-fluid state, said material being physically shaped by said walls into said curvilinear lens, said curvilinear shape of said lens minimizing optical distortion at each contiguous interface between adjacent zones of said lens; and removing said lens from said hollow of said die.

2. A method for forming a curvilinear lens by injection molding, the method comprising the steps of:

using a tool die to form a curvilinear lens by injection molding, the die capable of being parted;

defining a hollow in the die, the die having walls shaped to generally reflect an embodiment of the curvilinear lens, the embodiment comprising:
    a curvilinear first surface corresponding to an inner surface of the lens;
    a curvilinear second surface corresponding to an outer surface of the lens;
    a central zone positioned substantially at a center of the embodiment, the curvilinear second surface diverging with the curvilinear first surface about the central zone so that a thickness between the first surface and the second surface is generally maximized toward the center of the central zone;
    curvilinear side zones separated by the central zone, the side zones comprising:
        a first side zone contiguous to the central zone; and
        a second side zone contiguous to the central zone;

the curvilinear shape of the die being configured to minimize the optical distortion at each contiguous interface between zones of the lens formed thereby; and inserting a material into the hollow of the die to form the curvilinear lens.

3. A method for forming a curvilinear lens by injection molding, the method comprising the steps of:

using a tool die to form a curvilinear lens by injection molding, the die capable of being parted;

defining a hollow in the die, the die having walls shaped to generally reflect an embodiment of the curvilinear lens, the embodiment comprising:
    a curvilinear first surface corresponding to an inner surface of the lens;
    a curvilinear second surface corresponding to an outer surface of the lens;
    a central zone positioned substantially at a center of the embodiment, the curvilinear second surface diverging with the curvilinear first surface about the central zone so that a thickness between the first surface and the second surface is generally maximized toward the center of the central zone;
    curvilinear side zones separated by the central zone, the side zones comprising:
        a first side zone contiguous to the central zone; and
        a second side zone contiguous to the central zone,
    curvilinear rear zones spaced from the central zone by the side zones, the rear zones comprising:
        a first rear zone contiguous to the first side zone, wherein a curvature of the first side zone is substantially equal to a curvature of the first rear zone around the contiguous location; and
        a second rear zone contiguous to the second side zone, wherein a curvature of the second side zone is substantially equal to a curvature of the second rear zone around the contiguous location;

the die being shaped and configured to provide a curvilinear lens with minimal optical distortion at each contiguous interface of the lens zones; and inserting a material into the hollow of the die to form the curvilinear lens.

\* \* \* \* \*